United States Patent [19]

Hazard

[11] Patent Number: 4,978,212
[45] Date of Patent: Dec. 18, 1990

[54] OPTHALMOMETER
[75] Inventor: Edwin A. Hazard, Rochester, N.Y.
[73] Assignee: Amarel Precision Instruments, Inc., Fairport, N.Y.
[21] Appl. No.: 458,255
[22] Filed: Dec. 21, 1989
[51] Int. Cl.$^5$ ............................................. A61B 3/10
[52] U.S. Cl. ...................................... 351/212; 351/205
[58] Field of Search .............. 351/212, 205, 216, 217, 351/245

[56] References Cited
U.S. PATENT DOCUMENTS
3,969,019 7/1976 Nohda ................................ 351/212

Primary Examiner—Paul M. Dzierzynski
Attorney, Agent, or Firm—Martin Lukacher

[57] ABSTRACT

A binocular opthalmometer has rotatable imaging optics which provide an image of a referencing element (mire) to a binocular viewing assembly. The viewing assembly is held stable (horizontal) by referencing it to a fixed support or stand in which the rotatable optics are journaled. The referencing mechanism is provided by a shaft mounted for rotation about an axis radially spaced from the axis of rotation of the imaging optics and which is rotatably coupled at one end to the stationary support and at the other end to the viewing assembly.

14 Claims, 4 Drawing Sheets

OPTHALMOMETER

DESCRIPTION

The present invention relates to instruments for the measurement of the contour of the eye which are known as opthalmometers and are sometimes called keratometers, and particularly to opthalmometers having a rotatable measuring assembly which contains optics for forming an image of a reference or index known as a mire for viewing with an optical eyepiece assembly, wherein the optical eyepiece assembly is stabilized against rotation when the measuring assembly is rotated, thereby enabling a binocular eyepiece assembly to be used.

The invention is especially suitable for use in clinical opthalmology or optometry and whenever the radius of curvature, both in horizontal and vertical directions, of an eye of a subject is to be measured.

Curvature measuring opthalmometers contain an illuminated mire and prisms through which the reflection of the mire is transmitted. The prisms are rotated by calibrated wheels until images of the mire are superimposed. The amount of rotation is a measurement of the radius of curvature of the subject's eye. The optics, including the mire and prisms are known in the art, and reference may, for example, be had to Nohda, U.S. pat. No. 3,969,019 issued July 13, 1976 for further information with respect to the curvature measuring optics of opthalmometers.

Before curvature measurements are made by adjustment of the prisms of the opthalmometer's optics, the meridians of the measuring assembly must be aligned with the meridian of the eye by rotating the measuring assembly. Such rotation may obscure the measuring wheels and make reading of the calibrations on the wheels difficult. The requirement that the measuring assembly rotate makes the use of binocular eyepieces a practical impossibility since the binocular eyepieces would then be cocked at an angle to the horizontal (even perpendicular to the horizontal) and the viewer's head would have to be similarly cocked in order to use the opthalmometer.

The principal object of the present invention is to provide an improved opthalmometer having a mechanism for stabilizing the eyepiece assembly of the instrument against rotation when the measuring assembly is rotated, thereby permitting the use of binocular eyepieces.

It is a further object of the present invention to provide an improved opthalmometer in which the adjusting wheels which provide the measurements of the curvature of the cornea of the subject's eye are not obscured, by the post or support for the instrument, from observation by the user of the instrument.

Briefly described, an opthalmometer embodying the invention has a rotatable assembly of first optics for projecting light upon an eye of a subject and receiving light reflected from the cornea of the eye, which optics is adjustable for measurement of the curvature of the cornea. The opthalmometer has second optics (eyepiece optics) for viewing of an image resulting from the reflected light. A mechanism is provided for stabilizing the position in space of the viewing optics while the rotatable assembly of optics is rotated. The mechanism makes use of a support on which the rotatable mechanism is mounted for rotation about an axis. The viewing optics is provided by an assembly, which may include binocular eyepieces, and which is mounted for rotation relative to the measuring assembly about the axis of rotation of the measurement assembly. A shaft is rotatably disposed eccentrically of the axis. This shaft is rotatable with the measurement assembly. The shaft is coupled to the support on which the rotatable assembly is mounted (to a fixed reference) so that the shaft rotates as the measuring assembly rotates. The shaft is also coupled to the viewing assembly. Angular rotation of the measurement assembly is not transferred to the viewing assembly. Rather, the viewing assembly is stabilized in angular position, preferably with the binocular eyepieces along the horizontal meridian of the instrument. The eyepiece assembly is supported only by the rotatable measurement assembly. The support can be placed so that the wheels which adjust the prisms of the measuring assembly are not obscured from the viewing position which is located at the eyepiece end of the instrument.

The foregoing and other objects, features and advantages of the invention, as well as a presently preferred embodiment thereof, will become more apparent from a reading of the following description in connection with the accompanying drawings in which.

Figure 1:
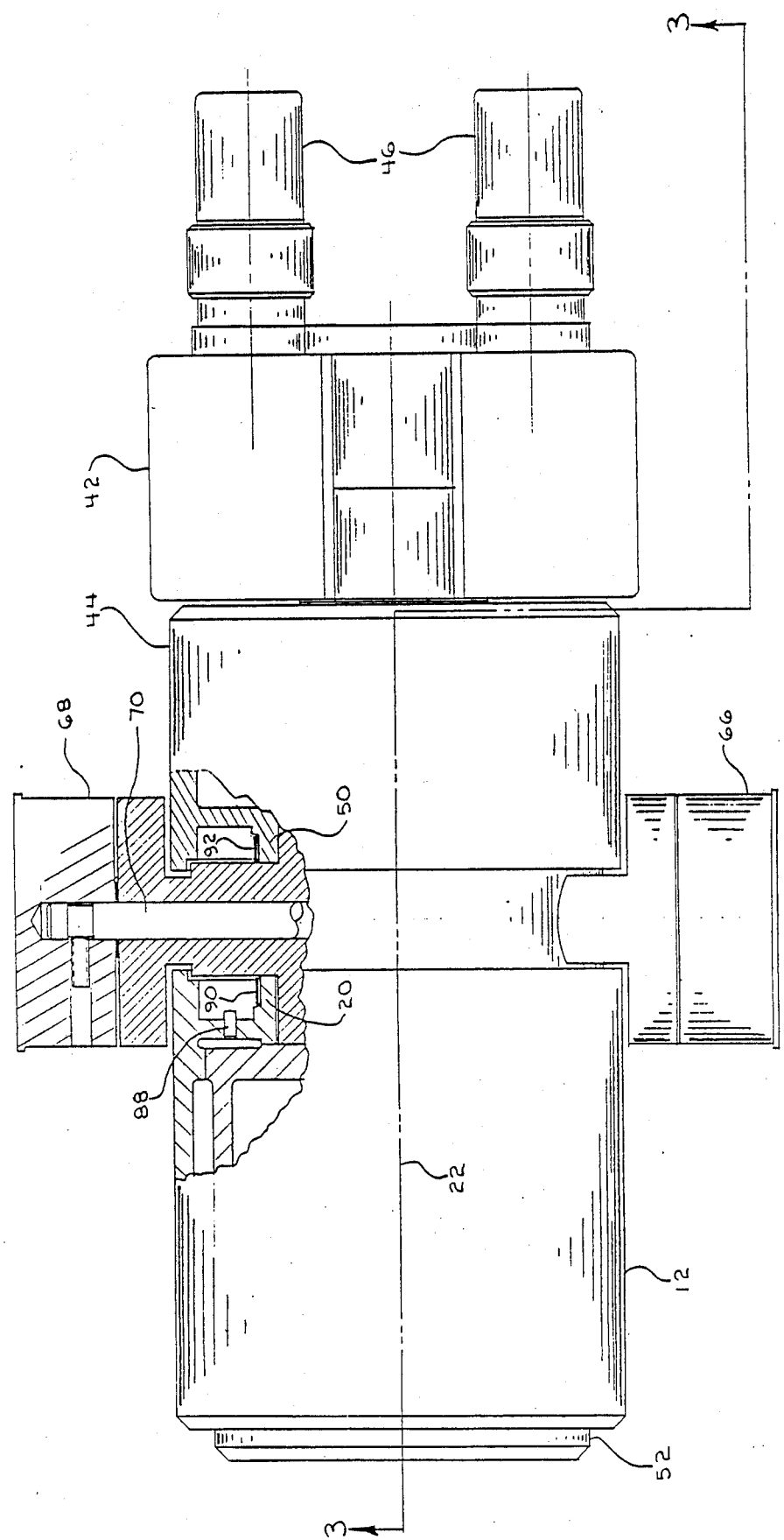
FIG. 1 is a plan view of an opthalmometer in accordance with the presently preferred embodiment of the invention, the view being partially broken away to illustrate the adjusting wheels of the measuring assembly of the instrument.
Figure 2:
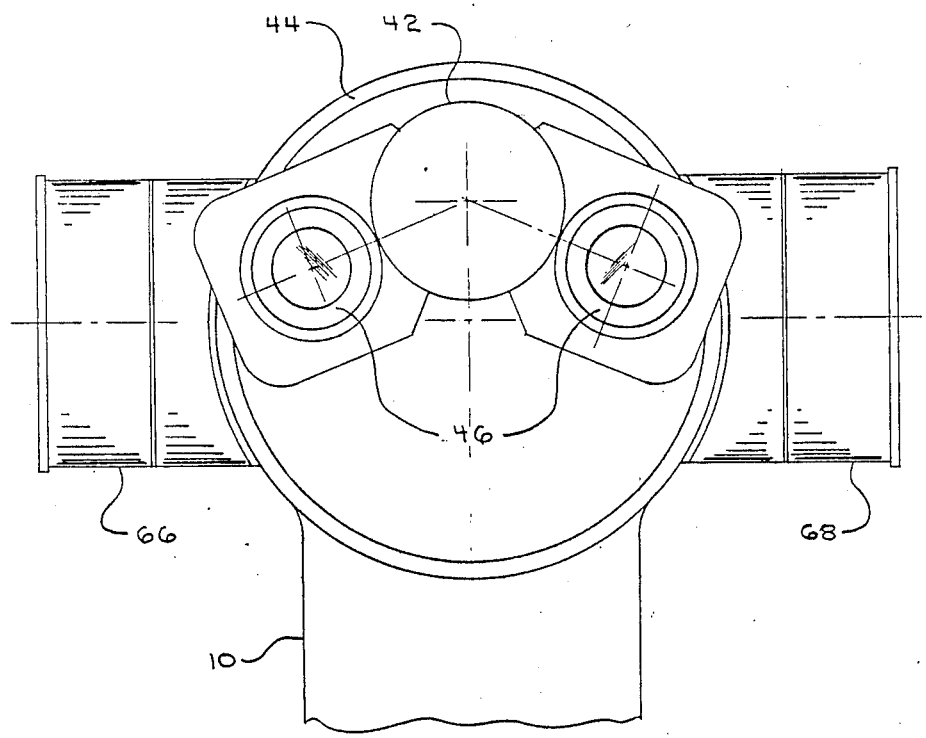
FIG. 2 is an end view from the right of the instrument shown in FIG. 1.
Figure 4:
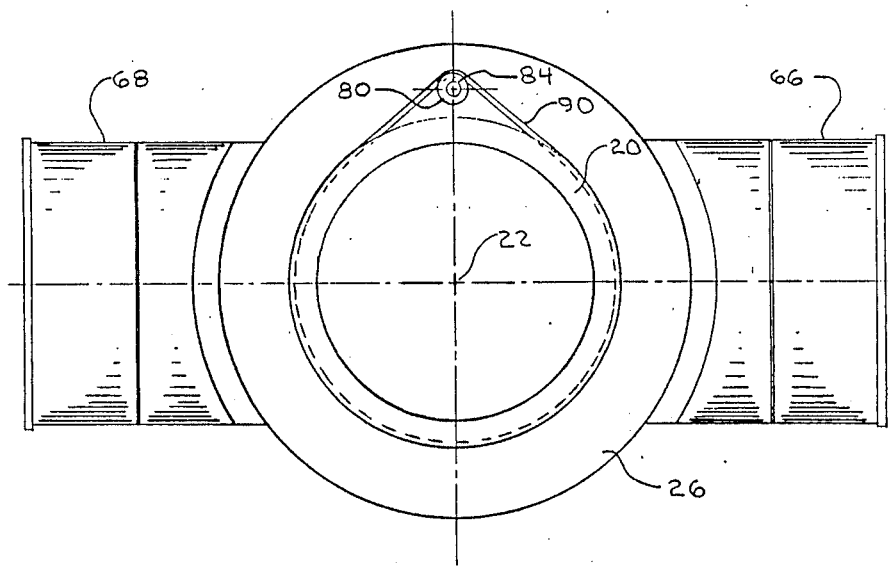
Figure 3:
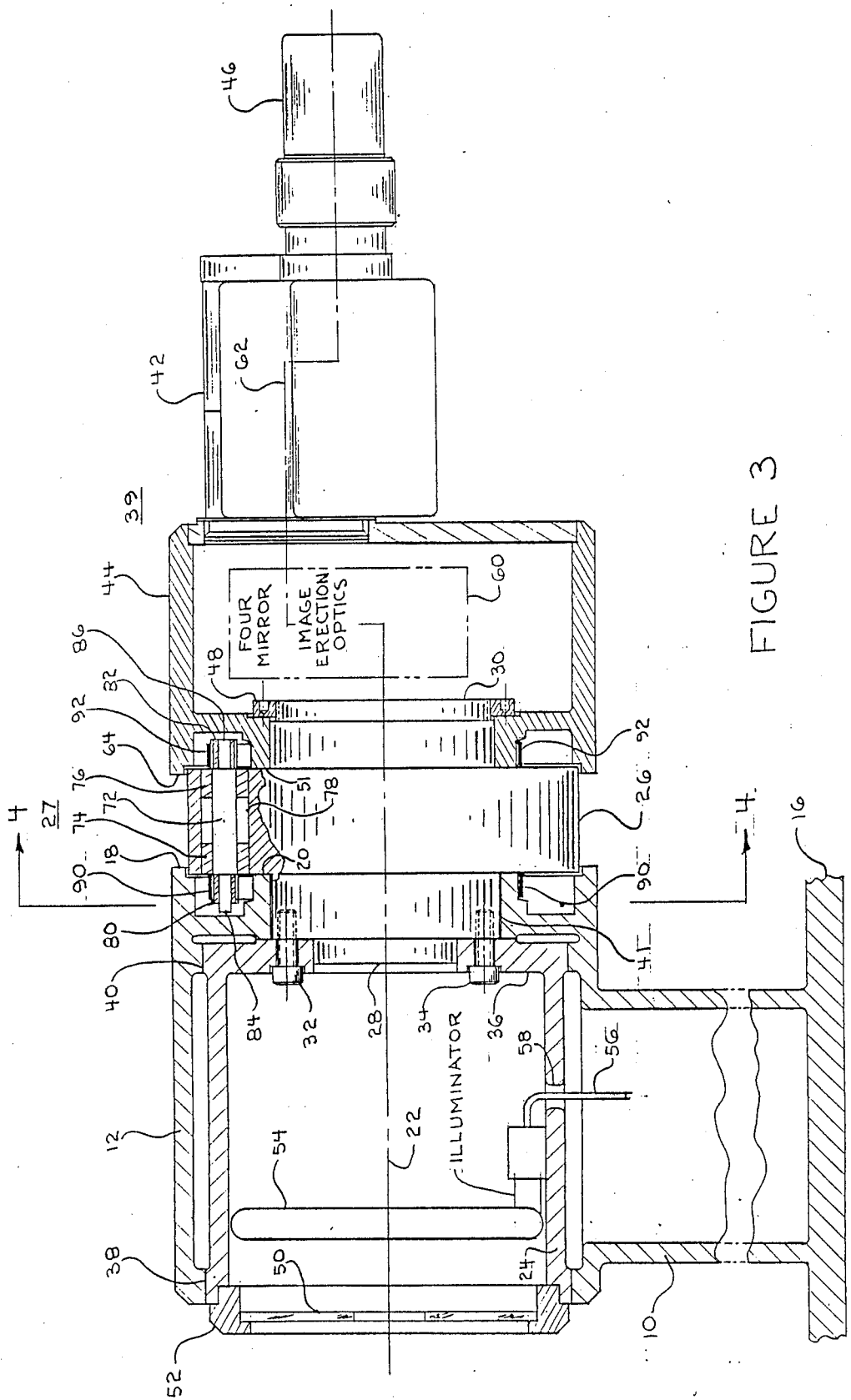
FIG. 3 is a sectional view of the instrument shown in FIGS. 1 and 2, the section being taken along the line 3—3 in FIG. 1.
Figure 5:
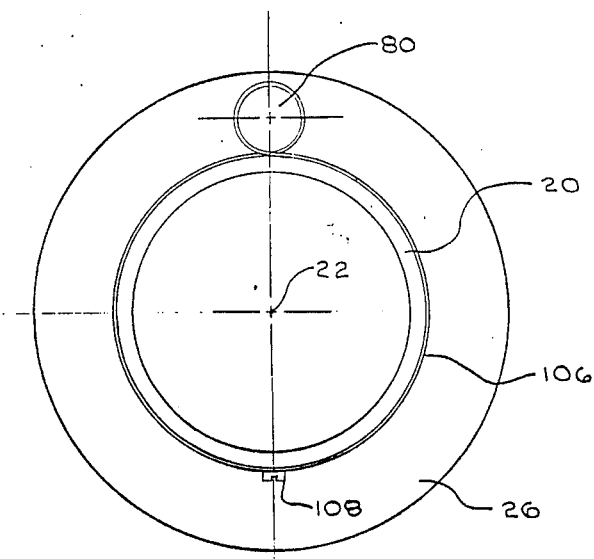
Figure 6:
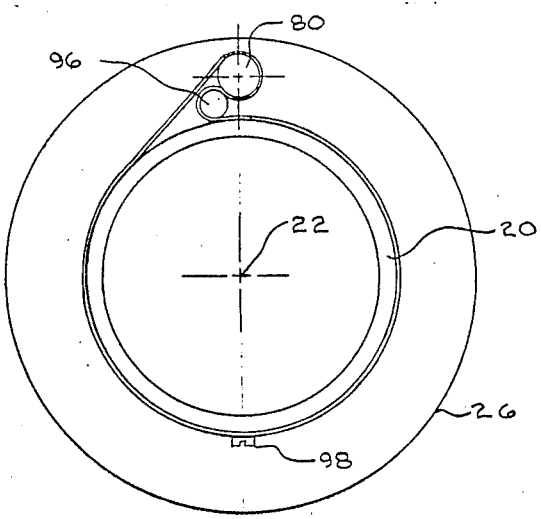
Figure 7:
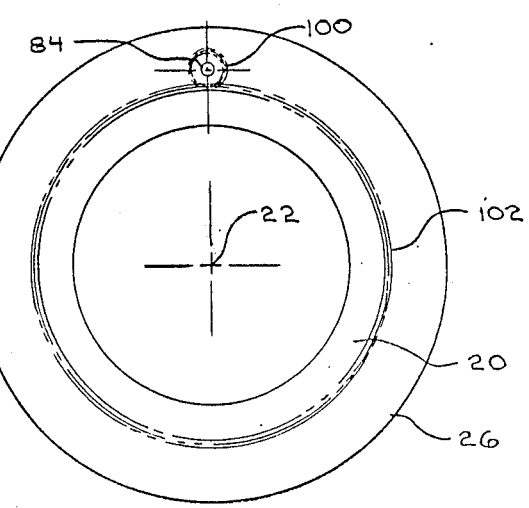

FIG. 4 is a sectional view of the instrument shown in FIGS. 1-3, the view being taken along the line 4—4 in FIG. 3; and FIGS. 5, 6 and 7 are views similar to FIG. 4, but without showing the adjustment wheels, which illustrate stabilizing mechanisms in accordance with embodiment of the invention other than shown in FIGS. 1 through 4.

Referring to FIGS. 1-4, there is shown a support 10 having a barrel 12 section and a section which extends downwardly to a base 16. The inner end of the support barrel 12 has outer and inner annular flanges 18 and 20. The outer periphery of the flange 20 defines a pulley the center of which is along a axis 22.

A rotatable imaging assembly 27, which contains the adjustable optics for forming an image of the cornea of the eye of a subject for measurements of the radii of curvature thereof, is located in an optical tube 24 and also in a barrel 26 having an inner end 28 and an outer end section 30. The inner end is connected by screws 32 and 34 to a flange 36 of the optical tube 24. The optical tube 24 is journaled within the support barrel 12 which provides annular bearing surfaces 38 and 40. The stepped inner end of the barrel 26 is preferably spaced from the inner periphery of the flange 20 of the support barrel 12 by a small clearance 41.

A viewing assembly 39 consists of a barrel 44 and a binocular head 42 to which binocular eyepieces 46 are attached. The binocular head includes conventional prisms for splitting an image which is provided by the rotatable optics in the rotatable assembly in the tube 24 and barrel 26. The viewing assembly 39 is cantilevered on the section 30 of the barrel 26. Inner flange 51 of the barrel 44 is retained by a ring 48 attached to section 30.

The optics of the rotatable assembly include a mire 50 mounted in a ring 52 at the forward end of the tube 24. An illuminator 54 having suitable lamps is also mounted in the tube and electrical leads 56 are brought out through an opening 58 in the tube 24. Since rotation of the tube and its assembly is limited to about 180°, there is sufficient slack in the leads 56 to prevent interference with such rotation. The barrel section 26 of the rotatable assembly contains lenses, an aperture plate and prisms, preferably a set of biasing prisms in addition to counter-rotating prisms such as shown in the above-reference Nohda patent. These optics form an image of the mire 50 which is reflected from the cornea of the subject's eye at an image plane within the binocular head 42. This image may be along the axis 22. An arrangement of four mirrors 60, which is of conventional design, is preferably used to erect the image wich is displaced vertically to the optical axis of the binocular head which is indicated at 62.

In addition to an inner flange 51, the barrel 44 also has an outer flange 64. The flange 51 is opposed to the flange 20 of the support 12 and the flange 64 is opposed to the flange 18 of that support. Between these flanges, the central part of the barrel 26, in which the lenses and prisms of the rotatable assembly are located, is disposed. The viewing assembly 39 is cantilevered from the barrel 26 and would be free to rotate about the axis 22 except for the stabilization mechanism described in detail below.

The rotatable assembly 39 may be rotated by knobs 66 and 68 which adjust the pairs of prisms in the barrel 26 by being connected to prism shifting mechanisms via shafts, one of which 70 from the knob or wheel 68 is shown. The knobs or wheels are calibrated either in millimeters or diopters or both to represent the radius of curvature and power along the horizontal meridian of the subject's eye for one wheel and the vertical meridian for the other wheel. Indices mounted on the knob support structure may be used to read the calibrations at the position to which the wheels 66 and 68 are turned when the alignment marks which are reflected from the cornea of the eye are viewed (by the opthalmologist or optometrist) using the binocular head 42.

Radially displaced from the axis 22, so that it is eccentric to the axis of rotation of the rotatable assembly, is a shaft 72. This shaft is journaled in bearings 74 and 76 in a hole 78 bored through the barrel 26. The shaft is rotatable independently about its own axis and rotates about the axis 22 when the rotatable assembly is rotated. This occurs on the initial alignment of the instrument with the power meridian of the patient's cornea, since the power meridian does not always occur at the horizontal and vertical axes of the eye.

At each end of the shaft 72 are pulleys 80 and 82. These pulleys may be pinned or otherwise captured on reduced diameter ends 84 and 86 of the shaft 72. The end 84 extends sufficiently far to be stopped by pins 88 which are approximately 180° apart and only one of which is shown in FIG. 1. These pins stop rotation of the rotatable assembly beyond approximately 180° (190°, for example, being suitable). The outer peripheries of the inner flanges 20 and 50 over which the pulleys 80 and 82 extend, define pulleys of much larger diameter than the shaft pulleys 80 and 82, and preferably of equal diameter to each other. The ratio of the diameter of the pulley 80 to the diameter of the flange 20 should be equal to the ratio of the pulley 82 diameter to the flange 51 diameter. The ends of these flanges 20 & 51 may be stepped so as to define flanges of the pulleys defined by these flanges 20 & 51. The smaller pulleys 80 and 82 on the shaft 72 may have teeth for receiving cleated timing belts 90 and 92.

The pulley defined by the outer periphery of the flange 20 is fixed because it is part of the support 12. Accordingly, as the rotatable assembly 27 is rotated, the belt 90 counter rotates with respect thereto, thereby rotating the pulley 80 and the shaft 72. This rotation is transferred by the pulley 82 and the belt 92 to the pulley defined by the outer periphery of the flange 51 on the viewing assembly 39. The head rotation and the rotation of the imaging optics, since the pulleys defined by the outer periphery of the flanges 20 and 51 are of the same diameter and the pulleys 80 and 82 are of the same diameter, are equal and opposite in angular extent. The viewing assembly 39 and its binocular head 42 remains stationary and horizontal in the position shown in the drawing. In effect, the viewing assembly 39 is referenced to the stationary housing by the stabilization mechanism of the belt, pulleys and shaft.

Referring to FIG. 6, there is shown a flexible band, for example, of non-elastic material which is tensioned around the pulleys 20 and 80. The tensioning is provided by a take-up roller 96. Since only approximately 180° of rotation is needed, a screw 98 may be used to permanently attach the flexible band of non-elastic material to the pulley 20.

FIG. 7 shows a gear system wherein the small pulleys 80 and 82 are replaced by spur gears 100. Gears 102 replace the pulleys defined by the outer peripheries of the flanges 20 and 50. The spur gears at opposite ends 84 and 86 of the shaft 72 have equal numbers of teeth and they mesh with larger gears 102 also having equal numbers of teeth.

Referring to FIG. 5, there is shown a flexible cable drive system wherein cables 106 are wrapped to form figure eights around the pulleys 80 and 82 and the pulleys defined by the outer peripheries of the flanges 20 and 50. A screw 108 may be used to fasten the cables as was the case for the screw 98 shown in FIG. 6.

From the foregoing description, it will be apparent that there has been provided an improved binocular opthalmometer, variations and modifications within the scope of the invention will undoubtedly suggest themselves to those skilled in the art. Accordingly, the foregoing description should be taken as illustrative and not a limiting sense.

I claim:

1. In an opthalmometer having a rotatable assembly of first optics for projecting light upon the eye of a subject and receiving light reflected from the cornea of the eye, which optics is adjustable for measurement of the curvature of the cornea, and having a second assembly of second optics for viewing of an image resulting from said reflected light, a mechanism for stabilizing the position in space of the assembly of viewing optics when said rotatable assembly of first optics is rotated, which mechanism comprises a support on which said first optics is mounted for rotation about an axis, means mounting said second optics for rotation relative to said first optics about said axis, a shaft rotatably disposed eccentrically of said axis and rotatable with said first optics, said shaft being coupled to said support for rotation as said first optics rotates, said shaft also being rotatably coupled to said second optics to stabilize said second optics in angular position with respect to said support while said first optics rotates.

2. The invention as set forth in claim 1 wherein said second optics comprises binocular viewing means.

3. The invention as set forth in claim 1 further comprising a first housing containing said first optics and being rotatably mounted on said support, a second housing supporting said second optics and being rotatably mounted on said first housing, pulleys on said shaft and rotatable therewith, a first pulley having its axis common with said axis and fixed to said support, a second pulley having its axis common to said axis and rotatable with said second housing, and belt means respectively coupling said pulleys on said shaft to said first and second pulleys.

4. The invention as set forth in claim 3 wherein said belt means are timing belts having cleats, at least said shaft pulleys having teeth engageable with said cleats.

5. The invention as set forth in claim 3, wherein said belts are flexible bands, and further comprising take-up rollers on said first housing adjacent to said shaft pulleys around which said bands are entrained for stretching and tensioning said bands.

6. The invention as set forth in claim 3 wherein said first and second pulleys are of the same diameter, and said pulleys on said shaft are of the same diameter.

7. The invention as set forth in claim 3 wherein said second housing is disposed at one end of said first housing, said support comprising a tubular structure in which said first housing is journaled, said tubular structure having an annular flange which defines said first pulley on the outer periphery thereof, said second housing having an annular flange opposed to the annular flange of said tubular structure, said last named flange having an outer periphery which defines said second pulley and which is of the same diameter as the outer periphery of said flange of said tubular structure, said pulleys on said shaft being disposed at the opposite ends of said shaft extending over said first and second pulleys, said pulleys on said shaft also being of the same diameter.

8. The invention as set forth in claim 7 wherein said first housing comprises a tube for containing a mire and illuminating means and a barrel disposed between said flanges for containing lenses and prisms of said first optics, said barrel having a hole radially spaced from said axis, said shaft being journaled in said hole.

9. The invention as set forth in claim 8 further comprising wheels mounted on said barrel and connected for adjusting the prisms of said first optics, a stand connected to said housing, said wheels being disposed between said stand and said second housing.

10. The invention as set forth claim 3 wherein said belt means are cables entrained around said pulleys on said shaft and said first and second pulleys respectively.

11. The invention as set forth in claim 3 wherein said second housing is disposed at one end of said first housing, said support comprising a tubular structure in which said first housing is journaled, said tubular structure having an annular flange, a first gear around the outer periphery of said flange, said second housing having an annular flange opposed to the annular flange of said tubular structure, said annular flange of said second housing having an outer periphery, a second gear along said outer periphery, said shaft having spur gears at the opposite ends thereof disposed in engagement with said first and second gears, respectively.

12. The invention as set forth in claim 1 further comprising a first housing containing said first optics and being rotatably mounted on said support, a second housing supporting said second optics and being rotatably mounted on said first housing, first and second gears respectively connected to said support and said second housing, each of said first and second gears having an axis common with said axis, and spur gears rotatable with said shaft and meshing respectively with said first and second gears.

13. The invention as set forth in claim 12 wherein said first and second gears have the same number of teeth, and said spur gears each have the same number of teeth.

14. The invention as set forth in claim 1 further comprising means on said support and said rotatable assembly including said first optics for limiting the rotation of said rotatable assembly to about 180°.

* * * * *